United States Patent [19]
Aoki et al.

[11] Patent Number: 5,512,298
[45] Date of Patent: Apr. 30, 1996

[54] CYTARABINE OCFOSFATE HARD CAPSULE

[75] Inventors: Minoru Aoki, Tokyo; Hiroshi Ohtaki, Yono; Nobuharu Fukui, Tokyo; Takashi Terada, Kousosu; Minoru Nakada, deceased, late of Kitamoto, all of Japan, by Tomoko Nakaka, heiress

[73] Assignee: Nippon Kayaku Kabushiki Kaisha, Tokyo, Japan

[21] Appl. No.: 36,509

[22] Filed: Mar. 24, 1993

[30] Foreign Application Priority Data

Apr. 3, 1992 [JP] Japan .................. 4-109053

[51] Int. Cl.⁶ .................. A61K 9/48; A61K 31/505
[52] U.S. Cl. .................. 424/452; 424/451; 514/49; 514/772.3; 514/778; 514/781; 514/908
[58] Field of Search .................. 514/49, 908, 772.3, 514/778, 781; 424/451, 452, 457

[56] References Cited

U.S. PATENT DOCUMENTS

| | | | |
|---|---|---|---|
| 3,859,431 | 1/1975 | Newton et al. | 424/37 |
| 4,542,021 | 9/1985 | Kodama et al. | 514/49 |
| 4,681,765 | 7/1987 | Guley | 424/456 |
| 4,812,560 | 3/1989 | Terada et al. | 536/29 |
| 5,049,663 | 9/1991 | Terada et al. | 536/29 |
| 5,223,503 | 6/1993 | Gossett et al. | 514/258 |

FOREIGN PATENT DOCUMENTS

| | | |
|---|---|---|
| 0239015 | 9/1987 | European Pat. Off. |
| 2924691 | 1/1980 | Germany |
| 8705804 | 10/1987 | WIPO |

OTHER PUBLICATIONS

Gennaro et al., "Remington's Pharmaceutical Sciences", Ionic Solutions and Electrolytic Equilibria: Pharmaceutical Significance, Chapter 17, Eighteenth Edition, 1990, pp. 245–246.

Remington's Pharmaceutical Sciences, pp. 1607 and 1625, 1985.

Chemical Abstracts, vol. 109, No. 12, 19 Sep. 1988, Columbus, Ohio, US; abstract No. 98727j, John E. Botzolakis et al.

Chemical Abstracts, vol. 103, No. 8, 26 Aug. 1985, Columbus, Ohio, US; Abstract No. 59243e, P. De Beukelaer et al.

*Primary Examiner*—Thurman K. Page
*Assistant Examiner*—Carlos Aspuru
*Attorney, Agent, or Firm*—Nields & Lemack

[57] ABSTRACT

The present invention relates to hard capsules of cytarabine ocfosfate which is useful as an anti-leukemia drug applicable to oral administration.

By providing the cytarabine ocfosfate hard capsule comprising (1) cytarabine ocfosfate, (2) a high molecular compound functioning as a disintegrator and (3) an alkali, there can be provided pharmaceutical preparations having excellent disintegration property and stability. The cytarabine ocfosfate hard capsules are applicable to clinical use.

7 Claims, No Drawings

CYTARABINE OCFOSFATE HARD CAPSULE

FIELD OF THE INVENTION

The present invention relates to hard capsules of cytarabine ocfosfate (4-amino-1-β-D-arabinofuranosyl- 2(1H)-pyrimidinone-5'-(sodium octadecyl phosphate)) which is useful as an oral anti-leukemia agent.

BACKGROUND OF THE INVENTION

Cytarabine ocfosfate (hereafter referred to as COP) is known in U.S. Pat. Nos. 4,812,560 and 5,049,663, etc. Capsules of arabinofuranosylcytosine- 5'-phosphate (Ara-CMP) are described in U.S. Pat. No. 4,542,021. In the pharmaceutical preparations, potato starch and lactose are added to prepare the capsules.

Where it is attempted to prepare COP into oral preparations such as capsules, etc. by adding starch and lactose thereto as in a conventional manner, the starch and lactose should be added to COP in considerably large amounts; where one needs to take COP in a dose necessary for treatment, the size of preparations so increases due to poor dispersibility that one can orally take the COP preparations only with difficulty. Further in order to disintegrate capsules satisfactorily, starch and lactose must be added in large quantities so that stability of COP is deteriorated and its decomposition products are formed; in this case, problems of decreased content of COP, etc. encounter. In addition, COP has a property that is extremely sparingly soluble in an acidic solution having pH below 4. A mere tabletting by compressing COP or encapsulation of COP results in a disadvantage that disintegration in an acidic solution is extremely retarded. Taking the physiological pH in the stomach into account, it is desired to provide pharmaceutical preparations capable of being readily disintegrated even in an acidic region.

An object of the present invention is to provide hard capsules which are excellent in stability of COP and do not impair their disintegrating property even in an acidic solution.

SUMMARY OF THE INVENTION

The present inventors have made extensive investigations to see if good disintegration property and stability of COP are both obtained by adding various additives to COP. As a result, it has been found that when a high molecular compound which acts as a disintegrator, especially a high molecular compound selected from low substituted hydroxypropyl cellulose, sodium carboxymethyl starch, partly pregelatinized starch and crosslinked polyvinylpyrrolidone is added to COP, hard capsules having excellent disintegration property which provide good stability of COP can be obtained. It has also been found that addition of an alkali further improves the stability. The present invention has thus been accomplished.

That is, the present invention relates to a cytarabine ocfosfate hard capsule comprising (1) cytarabine ocfosfate, (2) a high molecular compound which acts as a disintegrator and (3) an alkali.

DETAILED DESCRIPTION OF THE INVENTION

The present invention will be described in more detail. As the high molecular compound which acts as a disintegrator in the present invention, any high molecular compound may be used so long as it acts as a disintegrator and pharmaceutically acceptable. As such a high molecular compound there are a chemically modified starch, a cellulose derivative, a polyvinylpyrrolidone derivative, etc. Specific examples include low substituted hydroxypropyl cellulose, sodium carboxymethyl starch, partly pregelatinized starch, crosslinked polyvinylpyrrolidone, crosslinked sodium carboxymethyl cellulose, hydroxypropyl starch, etc. Among these high molecular compounds, preferred are low substituted hydroxypropyl cellulose, sodium carboxymethyl starch, partly pregelatinized starch and crosslinked polyvinylpyrrolidone. Further, more preferred are low substituted hydroxypropyl cellulose, sodium carboxymethyl starch and partly pregelatinized starch.

The low substituted hydroxypropyl cellulose exemplified as the high molecular compound used in the present invention is a cellulose which is substituted with hydroxypropyl in a low substitution degree, and may be the one as described in Japanese Pharmacopeia (1986) that has a propylation rate of the hydroxy group in the range of 7 to 16%. The sodium carboxymethyl starch is a water-soluble starch type high molecular compound which may be the one described in Standards for Ingredients of Drugs not in the Japanese Pharmacopeia (1986) and preferably has the carboxymethyl substitution degree of approximately 0.3 to 0.5.

The partly pregelatinized starch is starch which is converted into alpha-form and described in Standards for Ingredients of Drugs not in the Japanese Pharmacopeia (1986).

The crosslinked polyvinylpyrrolidone refers to a crosslinked non-water-soluble high molecular compound of vinylpyrrolidone and is commercially available under the name of, e.g, Kollidon CL (BASF).

The crosslinked sodium carboxymethyl cellulose refers to sodium carboxymethyl cellulose which is in part self-crosslinked and is exemplified by croscarmellose sodium, for example.

The hydroxypropyl starch refers to hydroxypropyl ether of starch and is specifically exemplified by the one described in Standards for Ingredients of Drugs not in the Japanese Pharmacopeia (1986).

These high molecular compounds which function as disintegrators are added to COP generally in the amount of approximately 0.5 to 4 parts by weight, preferably 1 to 3.5 parts by weight, more preferably 1.3 to 3.0 parts by weight, based on 1 part by weight of COP. The disintegrator may be used singly or in combination of two or more.

Turning to the alkali used in the present invention, there is no particular restriction to the alkali but any alkali may be used so long as it is usable as an additive for medical use. Specific examples of the alkali include sodium carbonate, potassium carbonate, sodium bicarbonate, sodium hydroxide, potassium hydroxide, etc. These alkalis may be used alone or in combination of two or more. It is generally preferred to use sodium carbonate or potassium carbonate. The alkali is added to COP generally in the amount of approximately 0.002 to 0.3 part by weight, preferably 0.005 to 0.2 part by weight, more preferably 0.007 to 0.07 part by weight, based on 1 part by weight of COP.

The components are packed in the hard capsule of the present invention in the following proportions: approximately 5 to 50 W/W %, preferably 10 to 47 W/W %, more preferably 20 to 40 W/W % of COP; 10 to 80 W/W %, preferably 15 to 75 W/W %, more preferably 30 to 70 W/W % of the high molecular compound acting as a disintegrator; and 0.1 to 8.0 W/W %, preferably 0.2 to 4.0 W/W % of the alkali. The balance is other additives and these additives are incorporated in the amount of approximately 0 to 84 W/W %, preferably 1 to 74 W/W %.

In order to obtain the hard capsule of the present invention, other suitable additives, for example, excipients, binders and lubricants may also be packed in the hard capsule. Examples of the excipient include starch such as corn starch, potato starch, wheat flour, etc., and sugars such as lactose, mannitol, glucose, etc. The excipient may be added to COP in the amount of approximately 0.5 to 7 parts by weight, preferably 1 to 5 parts by weight, based on 1 part by weight of COP.

Examples of the binder include water-soluble cellulose ester derivatives such as hydroxypropyl cellulose, methyl cellulose, etc. and polyvinylpyrrolidone, sodium alginate, starch glue, aminoalkyl methacrylate copolymer (Eudragit), gum arabic, etc. The binder may be added to COP in the amount of approximately 0.005 to 0.2 part by weight, preferably 0.01 to 0.1 part by weight, based on 1 part by weight of COP.

As the lubricant there are used stearic acid and stearates such as magnesium stearate, etc., talc, leucine, carnauba wax, cacao butter, polyethylene glycol, cetanol, paraffin, etc. The lubricant may be added to COP in the amount of approximately 0.005 to 0.10 part by weight, preferably 0.009 to 0.05 part by weight, based on 1 part by weight of COP.

COP used for the preparation of the hard capsule of the present invention is a non-hygroscopic and stable crystal disclosed in U.S. Pat. Nos. 4,812,560 and 5,049,663. For packing the respective components into capsules, the components are generally granulated by wet granulation or dry granulation and then packed in capsules to obtain the hard capsules of the present invention.

The wet granulation is a method which comprises uniformly blending COP and the additives, kneading the blend in a suitable solvent, granulating, drying and grinding the granules, etc., if necessary, to a suitable diameter, generally below 8 mesh, preferably below 20 mesh. As the solvent, there may be used, for example, ethanol, methanol, acetone, ethyl acetate, dichloroethane, cyclohexane, etc. In view of the residual solvent, ethanol is desirable and hydrated ethanol is more desirable, taking safety in handling into consideration.

The dry granulation refers to a method which comprises uniformly blending COP and the additives, compressing and molding the blend into a flake-like or pellet-like shape, and grinding the compressed mold granules, etc. to a suitable diameter, generally below 8 mesh, preferably below 20 mesh.

Hereafter the present invention will be specifically described by referring to the examples below.

EXAMPLE 1

After 25 parts of COP, 35 parts of low substituted hydroxypropyl cellulose (Shin-Etsu Kagaku: L-HPC), 55 parts of mannitol, 68 parts of potato starch, 2 parts of hydroxypropyl cellulose and 4 parts of sodium carbonate are blended, the blend is kneaded with 60% ethanol and granulated. The granules are dried at 50° C. After drying, the granules are ground into those below 20 mesh followed by incorporating 1 part of magnesium stearate. Thereafter 190 mg of the mixture is packed in a hard capsule of No. 3 to obtain the hard capsule of the present invention.

EXAMPLE 2

After 50 parts of COP, 80 parts of low substituted hydroxypropyl cellulose .(Shin-Etsu Kagaku: L-HPC), 55 parts of mannitol, 2 parts of methyl cellulose and 2 parts of sodium carbonate are blended, the blend is kneaded with 70% ethanol and granulated. The granules are dried at 60° C. After drying, the granules are ground into those below 16 mesh followed by incorporating 1 part of magnesium stearate. Thereafter 190 mg of the mixture is packed in a hard capsule of No. 3 to obtain the hard capsule of the present invention.

EXAMPLE 3

After 50 parts of COP, 150 parts of partly pregelatinized starch (Asahi Chemical: PCS), 4 parts of polyvinylpyrrolidone and 2 parts of sodium carbonate are blended, the blend is compact-molded into a flake-like shape using a dry granulator (Turbo Industry: Roller Compacter) followed by grinding into granules below 20 mesh. Further 1 part of stearic acid is added to the granules, 207 mg of the mixture is packed in a hard capsule of No. 3 to obtain the hard capsule of the present invention.

EXAMPLE 4

After 100 parts of COP, 220 parts of crosslinked polyvinylpyrrolidone (BASF: Kollidon CL) and 3 parts of sodium carbonate are blended, the blend is compact-molded into a flake-like shape using a dry granulator (Turbo Industry: Roller Compacter) followed by grinding into granules below 20 mesh. Further 2 parts of talc is added to the granules, 325 mg of the mixture is packed in a hard capsule of No. 1 to obtain the hard capsule of the present invention.

EXAMPLE 5

After 100 parts of COP, 165 parts of low substituted hydroxypropyl cellulose (Shin-Etsu Kagaku: L-HPC), 1 part of sodium carbonate and 3 parts of hydroxypropyl cellulose are blended, the blend is kneaded with 70% ethanol and granulated. The granules are dried at 60° C. After drying, the granules are ground into those below 16 mesh followed by incorporating 1 part of magnesium stearate. Thereafter 270 mg of the mixture is packed in a hard capsule of No. 2 to obtain the hard capsule of the present invention.

EXAMPLE 6

After 25 parts of COP, 35 parts of sodium carboxymethyl starch, 55 parts of mannitol, 68 parts of potato starch, 2 parts of hydroxypropyl cellulose and 4 parts of sodium carbonate are blended, the blend is kneaded with 60% ethanol and granulated. The granules are dried at 50° C. After drying, the granules are ground into those below 20 mesh followed by incorporating 1 part of magnesium stearate. Thereafter 190 mg of the mixture is packed in a hard capsule of No. 3 to obtain the hard capsule of the present invention.

Next, the disintegration property and stability of the hard capsule according to the present invention were examined.

Experiment 1: Test on Disintegration

A time period for disintegration of 6 hard capsules of the present invention for each group was examined by a modified method of the disintegration test described in Japanese Pharmacopeia (1986), using a device for disintegration test. First fluid (prepared by adding 24.0 ml of diluted hydrochloric acid and water to 2.0 g of sodium chloride to dissolve sodium chloride and adding water to make the volume 1000 ml; pH is about 1.2) was used as a test solution and measurement was performed at 37° C. of the solution temperature. The results are shown in Table 1.

TABLE 1

| Sample | Time Require for Disintegration (average) |
| --- | --- |
| Hard capsule of Example 1 | 3 minutes and 50 seconds to 6 minutes and 40 seconds (5 minutes and 13 seconds) |
| Hard capsule of Example 2 | 4 minutes and 20 seconds to 6 minutes and 40 seconds (5 minutes and 22 seconds) |
| Hard capsule of Example 3 | 3 minutes and 18 seconds to 3 minutes and 45 seconds (3 minutes and 25 seconds) |
| Hard capsule of Example 4 | 3 minutes and 35 seconds to 4 minutes and 20 seconds (3 minutes and 53 seconds) |
| Hard capsule of Example 5 | 5 minutes and 00 seconds to 8 minutes and 00 seconds (6 minutes and 15 seconds) |
| Hard capsule of Example 6 | 3 minutes and 05 seconds to 3 minutes and 57 seconds (3 minutes and 29 seconds) |

The hard capsules of the present invention all shows excellent disintegration property, indicating that the time for disintegration was within 10 minutes. The results show that the pharmaceutical preparations having good disintegration property even at the physiological pH in the stomach, i.e., even in an acidic region can be obtained.

Experiment 2: Test on Stability

With respect to stability of the hard capsule according to the present invention, the following tests were carried out under severe conditions and under storage for a long period of time.

1. Severe Conditions

The hard capsules of the present invention and a capsule for control were stored for 30 days under severe conditions at 65° C. under relative humidity of 73%. Then the content of cytarabine ocfosfate was assayed. The content was determined based on an area percentage of cytarabine ocfosfate and its decomposition products by liquid chromatography. The results are shown in Table 2.

TABLE 2

| Sample | Content (%) |
| --- | --- |
| Hard capsule of Example 1 | 100.0 |
| Hard capsule of Example 2 | 100.0 |
| Hard capsule of Example 3 | 100.0 |
| Hard capsule of Example 5 | 100.0 |
| Hard capsule of Example 6 | 100.0 |
| Hard capsule for comparison* | 87.5 |

* Composition of the hard capsule for comparison:

After 10 parts of COP, 50 parts of crystalline cellulose, 3 parts of magnesium stearate, 100 parts of lactose and 100 parts of potato starch are blended, 263 mg each of the blend is packed in capsules to prepare capsules.

The content of COP in the hard capsule according to the present invention showed 100%. On the other hand, that in the hard capsule for comparison decreased significantly to 87.5%.

2. Storage over a Long Period of Time

After the hard capsules of the present invention were stored at room temperature for 42 months, the content of COP was determined. No reduction in the content was noted in any of the hard capsules of the present invention.

As is clearly noted from the foregoing results, the hard capsules of the present invention provide pharmaceutical preparations having excellent disintegration property and stability, by incorporating the high molecular compound functioning as a disintegrator and the alkali. In addition, a high dose of COP per preparation can be provided according to the present invention. The high dose COP preparation is useful for clinical application.

What is claimed is:

1. A cytarabine ocfosfate hard capsule comprising (1) cytarabine ocfosfate, (2) a high molecular compound functioning as a disintegrator Selected from the group consisting of a hydroxypropyl cellulose having a propylation rate of the hydroxy group in the range of 7% to 16%, sodium carboxymethyl starch, pregelatanized starch and crosslinked polyvinylpyrrolidone; and (3) an alkali.

2. A hard capsule according to claim 1, wherein said high molecular compound functioning as a disintegrator is selected from the group consisting of a hydroxypropyl cellulose having a propylation rate of the hydroxy groups in the range of 7% to 16%, sodium carboxymethyl starch and pregelatinized starch.

3. A hard capsule according to claim 1, wherein said high molecular compound functioning as a disintegrator is incorporated in an amount of 0.5 to 4 parts by weight based on 1 part by weight of cytarabine ocfosfate.

4. A hard capsule according to claim 1, wherein said alkali is incorporated in an amount of 0.002 to 0.3 part by weight based on 1 part by weight of cytarabine ocfosfate.

5. A hard capsule according to claim 1, wherein said high molecular compound functioning as a disintegrator is incorporated in an amount of 10 to 80 W/W % based on the weight of the composition.

6. A hard capsule according to any one of claims 1, and 3, wherein a proportion of each component is in the range of (1) 5 to 50 W/W % in cytarabine ocfosfate, (2) 10 to 80 W/W % in the high molecular compound functioning as a disintegrator, and (3) 0.1 to 8.0 W/W % in the alkali.

7. A hard capsule comprising (1) 5 to 50 W/W % of cytarabine ocfosfate, (2) 10 to 80 W/W % of a hydroxypropyl cellulose having a propylation rate of the hydroxy groups in the range of 7% to 16%, and (3) 0.1 to 8.0 W/W % of sodium carbonate in terms of a proportion based on the weight of the composition.

* * * * *